United States Patent [19]
Richter et al.

[11] Patent Number: 5,866,105
[45] Date of Patent: Feb. 2, 1999

[54] PHARMACEUTICAL COMPOSITION

[75] Inventors: Friedrich Richter, Schönbühl; Marianne Roser, Bern, both of Switzerland

[73] Assignee: Novartis AG, Basel, Switzerland

[21] Appl. No.: 466,490

[22] Filed: Jun. 6, 1995

Related U.S. Application Data

[63] Continuation of Ser. No. 272,711, Jul. 8, 1994, abandoned, which is a continuation of Ser. No. 48,153, Apr. 14, 1993, abandoned, which is a continuation of Ser. No. 886,797, May 21, 1992, abandoned.

[30] Foreign Application Priority Data

May 23, 1991 [GB] United Kingdom ............... 9111210
Mar. 2, 1992 [GB] United Kingdom ............... 9204472

[51] Int. Cl.⁶ ............................. A61K 7/043; A61K 7/04
[52] U.S. Cl. ................................. 424/61; 514/858
[58] Field of Search .................... 424/61; 514/858

[56] References Cited

U.S. PATENT DOCUMENTS

| | | | |
|---|---|---|---|
| 4,755,534 | 7/1988 | Stuetz | 514/655 |
| 4,920,109 | 4/1990 | Onishi et al. | 514/460 |
| 4,957,730 | 9/1990 | Bohn | 424/61 |
| 5,057,312 | 10/1991 | Langlia | 424/61 |
| 5,106,878 | 4/1992 | Guerry et al. | 514/651 |
| 5,116,603 | 5/1992 | Friedman | 514/900 |
| 5,120,530 | 6/1992 | Ferro | 424/61 |
| 5,132,459 | 7/1992 | Stuetz | 564/387 |
| 5,160,737 | 11/1992 | Friedman | 424/49 |

FOREIGN PATENT DOCUMENTS

| | | |
|---|---|---|
| 0298271 | 1/1989 | European Pat. Off. . |
| 0399858 A1 | 11/1990 | European Pat. Off. . |
| 2002795 | 2/1979 | United Kingdom . |
| 2197194 | 5/1988 | United Kingdom . |
| 8702580 | 5/1987 | WIPO . |
| 8806884 | 9/1988 | WIPO . |

OTHER PUBLICATIONS

G. Petranyi et al., Antimicrobial Agents and Chemotherapy, vol. 31, No. 10, 1987, pp. 1558–1561.
Merck Index, 11th edition, 1989, p. 1442.
R. Savin, Clinical and Experimental Dermatology, vol. 14, 1989, pp. 116–119.
V. Villars and TC Jones, Journal of Dermatological Treatment, vol. 1, Suppl. 2, 1990, pp. 33–38.
TC Jones, Journal of Dermatological Treatment, vol. 1, Suppl. 2, 1990, pp. 29–32.

*Primary Examiner*—Sally Gardner-Lane
*Attorney, Agent, or Firm*—Carol A. Loeschorn

[57] ABSTRACT

The invention concerns topical formulations such as nail varnishes comprising as the active agent the compound of formula I

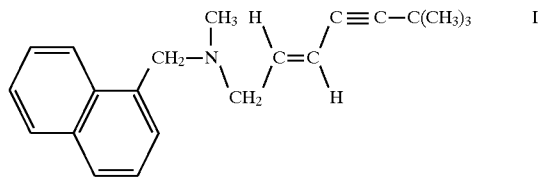

in free base form or in acid addition salt form, together with a polymeric film former and further excipients as appropriate. It also concerns a process of preparation of such preparations by mixing with an appropriate polymeric film former and conventional further excipients as appropriate, and a method of treatment of onychomycosis.

9 Claims, No Drawings

PHARMACEUTICAL COMPOSITION

This is a continuation of application Ser. No. 08/272,711, filed Jul. 8, 1994, which in turn is a continuation of application Ser. No. 08/048/153, filed Apr. 14, 1993, which in turn is a continuation of application Ser. No. 07/886,797, filed May 21, 1992, all of which are now abandoned.

The present invention relates to topical formulations containing an allylamine compound as the pharmacologically active agent.

It concerns a topical formulation such as a a nail varnish comprising as the active agent the compound of formula I

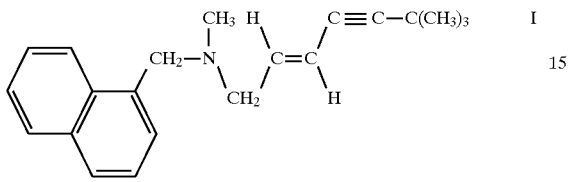

in free base form or in acid addition salt form, together with a polymeric film former such as polyvinyl acetate, acrylic- and methacrylic-acid alkyl ester copolymerisates with quaternary ammonium groups or methylvinylether-maleic acid monoalkyl ester copolymerisates and further excipients as appropriate.

The compound of formula I may be in free base form or in acid addition salt form. An acid addition salt form may be prepared from the free base form in conventional manner and vice-versa. Examples of suitable acid addition salt forms are the hydrochloride, the lactate and the ascorbate. The free base and the hydrochloride are preferred.

The compound of formula I is known from e.g. EP-A-24587. It belongs to the class of allylamine anti-mycotics. It is known in the art under its generic name as terbinafine, and it is commercially available under the trademark LAMISIL®. Apart from its efficacy against dermatophytes after oral as well as topical administration, we have found, it is also highly efficient after oral application in the treatment of onychomycosis, as it has a strong fungicidal activity and high affinity to the keratin of the nails, where it is enriched. Therefore a significantly higher cure rate may be achieved than with conventional therapies such as e.g. oral treatment with griseofulvin.

Although the compound of formula I is a very safe drug, systemic treatment of onychomycosis offers some disadvantages, e.g. exposure of the whole organism to the drug substance and the need for rather high doses. Therefore, the possibility of local, namely topical, treatment is highly desirable and would be preferred by many patients. On the other hand, many attempts have been made with various drugs, e.g. griseofulvin, to prepare topical formulations for the treatment of onychomycosis but the results obtained were unconvincing. This might be related to insufficient penetration of the drugs into the deeper layers of the nails.

It has now been found that the compound of formula I, when it is formulated in the proper vehicle, is surprisingly highly efficient upon topical application to infected nails in the treatment of onychomycosis.

Such formulations should ideally have the following properties:
  As penetration into the infected nails is a rather slow process, they should build up a depot after application from where the drug can freely diffuse into the nail tissue;
  they should have the capacity to easily release the drug;
  they should be comfortable for the patient, e.g. easy to apply, to be applied with low frequency, easy to remove and well tolerated.

It has been found that such formulations can be obtained with the benefits mentioned above and a high efficacy by formulating the compound of formula I in free base form or in acid addition salt form as a nail varnish containing one or more suitable film formers and conventional further excipients as appropriate.

Components of the nail varnishes of the invention are:
  1. The compound of formula I in free base form or in acid addition salt form.
  2. A polymeric film former. This may be either water-soluble or water-insoluble. Polymers suitable as water-insoluble film formers are e.g. polyvinylacetate, acrylic- and methacrylic-acid alkyl ester copolymerisates with quaternary ammonium groups and methylvinylether-maleic acid monoalkyl ester copolymerisates. Whereas the polymer most frequently used in nail varnishes is nitrocellulose, this polymer cannot be used in the present invention due to chemical incompatibility with the drug substance. Polymers suitable as water-soluble film formers are in particular polymers soluble in water as well as in organic solvents. Such polymers are e.g. polyvinylpyrrolidone (PVP) and vinylpyrrolidone-vinyl acetate copolymers. Preferably the mean molecular weight of these copolymers is about 60,000±15,000. A commercially available polymer of the latter class is e.g. known under the tradename KOLLIDON VA 64. Preferred are water-insoluble film formers such as polyvinyl acetate or acrylic- and methacrylic-acid alkyl ester copolymerisates with quaternary ammonium groups as e.g. available under the tradenames EUDRAGIT RL and EUDRAGIT RS resins or methylvinylether-maleic acid monoalkyl ester copolymerisates as e.g. available under the tradename GANTREZ ES.

The compound of formula I and the polymeric film former are preferably present in the composition in the proportion of from about 1:0.5 to about 1:25, more preferably of from about 1:1 to about 1:20 and most preferably of from about 1:1 to about 1:10 on a w/w basis.

The compound of formula I makes up from e.g. about 0.5% to about 30%, preferably from about 1% to about 20% of the total composition on a weight basis.

In addition to the drug substance and the polymeric film former the compositions normally contain conventional further excipients, e.g. a solvent system. This can be either aqueous or organic or a mixture between organic solvents and water. Organic solvents are those which are physiologically acceptable and compatible with the drug substance and the further ingredients of the composition. Typical solvents are ethanol, isopropanol, acetone and ethyl acetate. The preferred solvent system is ethanol, with the addition of a certain amount of water. The amount of water is in most cases less than the amount of the solvents. Typical water/solvent ratios are e.g. below 1:3. However in some cases the amount of water may exceed that of the solvent. It may then be e.g. up to 2.5:1.

The compositions of the invention usually also contain additional ingredients which stabilize the formulations and improve their properties. In particular such further excipients are:
  plasticizers such as dialkylphthalates, e.g. dibutylphthalate, hydroxy-fatty acid oils, e.g. castor oil, triglycerides and silicon oils;
  film modifiers which change the properties of the main film former, in particular improve its application properties, e.g. hardness after evaporation of the solvent or flexibility on the nail. These modifiers can be e.g. acrylic ester resins, arylsulfonamide-formaldehyde resins, cellulose derivatives or polyamide resins;

surfactants, e.g. polyethylenglycol-alkylethers (e.g. as available under tradename BRIJ), which help solubilize the drug especially in vehicles containing water;

penetration enhancers, e.g. azole, dimethylsulfoxide, unsaturated fatty alcohols, surfactants and propylene glycol;

colouring agents;

antioxidants, e.g. tocopherol;

complexing agents, e.g. ethylenediaminetetraacetic acid (Komplexon III); and

UV-absorbers.

The topical formulations of the invention such as nail varnishes can be obtained by a process comprising mixing the compound of formula I in free base form or in acid addition salt form with an appropriate polymeric film former such as polyvinyl acetate or acrylic- and methacrylic-acid alkyl ester copolymerisates with quaternary ammonium groups or methylvinylether-maleic acid monoalkyl ester copolymerisates and further excipients, e.g. the solvent system, as appropriate. The process of the invention may be effected in conventional manner.

The compositions according to the invention are especially useful for the treatment of onychomycosis. An indicated daily dose to be administered typically is from about 0.05 to about 5.0 mg of the compound of formula I per square centimeter of the treated nail material. Preferred application rates are from about 0.1 to 3.0 mg per square centimeter. The concentration of the compound of formula I in the tissue at the place of action is preferably e.g. between 0.001 and 1.0 mg/g depending on the type of fungal nail infection and type of treated nails. Applications may take place once a day in severe cases or even only once a week. Preferably treatments are repeated every second or third day.

Both the nail material at fingers and toes may be treated when infected with fungi causing onychomycosis, e.g. dermatophytes, yeast fungi or molds.

The following examples illustrate the invention (the compound of formula I is herein briefly named compound 1):

EXAMPLE 1

Nail Varnish 20%

| Ingredient | Amount (g/100 g) |
| --- | --- |
| Compound 1 in free base form | 20.00 |
| Dibutyl phthalate | 0.70 |
| Acrylic resin, hard durable (e.g. PARALOID A-21) | 2.50 |
| Polyvinyl acetate | 13.50 |
| Ethyl acetate | 63.30 |
| Example 2: Nail varnish 5% | |
| Compound 1 in free base form | 5.0 |
| Dibutyl phthalate | 0.6 |
| 50% solution of a copolymerisate of methyl-vinylether and maleic acid monobutyl ester in ethanol (e.g. GANTREZ ES 425) | 30.0 |
| Ethanol | 30.0 |
| Ethyl acetate | 34.4 |
| Example 3: Nail varnish 5% | |
| Compound 1 in free base form | 5.0 |
| Glycerol triacetate | 2.0 |
| Oleic alcohol | 2.0 |
| 50% solution of a copolymerisate of methyl-vinyl-ether and maleic acid mono-ethyl ester in ethanol (e.g. GANTREZ ES 225) | 40.0 |
| Water | 10.0 |
| Ethanol 94% W/W | 40.98 |
| Butyl hydroxytoluene | 0.02 |
| Example 4: Nail varnish 5% | |
| Compound 1 in hydrochloride form | 5.0 |
| Glycerol triacetate | 2.0 |
| Isopropyl myristate | 2.0 |
| GANTREZ ES 225 | 40.0 |
| Water | 10.0 |
| Ethanol 94% W/W | 40.98 |
| Butyl hydroxytoluene | 0.02 |
| Example 5: Nail varnish 5% | |
| Compound 1 in hydrochloride form | 5.0 |
| Glycerol triacetate | 2.0 |
| Isopropyl myristate | 2.0 |
| copolymerisate of acrylic- and methacrylic-acid esters with a small amount of quaternary ammonium groups (e.g. EUDRAGIT RL 100) | 20.0 |
| Acrylic resin, hard durable (e.g. PARALOID B-82) | 2.5 |
| Water | 5.0 |
| Ethanol 94% W/W | 63.48 |
| Butyl hydroxytoluene | 0.02 |
| Example 6: Nail varnish 2% | |
| Compound 1 in hydrochloride form | 2.0 |
| Castor oil | 3.0 |
| 50% solution of a copolymerisate of methyl-vinylether and maleic acid mono-butyl ester in ethanol (e.g. GANTREZ ES 425) | 40.0 |
| Ethanol 94% W/W | 55.0 |
| Example 7: Nail varnish 10% — water removable | |
| Compound 1 in hydrochloride form | 10.0 |
| Isopropyl myristate | 6.0 |
| Vinylpyrrolidone-vinylacetate-copolymer | 12.0 |
| Water | 5.0 |
| Isopropanol | 67.0 |
| Example 8: Nail varnish 5% — water removable | |
| Compound 1 in hydrochloride form | 5.0 |
| Isopropyl myristate | 6.0 |
| Vinylpyrrolidone-vinylacetate-copolymer | 10.0 |
| Isopropanol | 79.0 |
| Example 9: Nail solution 1% — aqueous — water removable | |
| Compound 1 in hydrochloride form | 1.0 |
| Polyoxyethylene-4-lauric alcohol (e.g. BRIJ 30) | 2.0 |
| Vinylpyrrolidon-vinylacetate-copolymer | 12.0 |
| 1,2-Propylene glycol | 5.0 |
| Ethanol 94% W/W | 25.0 |
| Sodium pyrosulfite | 0.1 |
| Na-EDTA | 0.1 |
| Distilled water | 54.8 |

The efficacy of the formulations of the invention can be shown in vitro or in vivo. A suitable in vitro method is measurement of the penetration through excised nails where it can be shown that fungicidally effective concentrations of the drug are reached also in deeper layers of the nail tissue. A further in vitro method is the measurement of the dissolution rate of the drug from a dried varnish layer where it can be shown that fungicidally effective amounts of the drug are sufficiently released from dried varnish layers. In vivo the most convincing test is the double blind study with onychomycosis.

We claim:

1. A method for the treatment of onychomycosis comprising administering a topical nail varnish formulation to the nails of a patient in need of such treatment, wherein said nail varnish formulation comprises 1) a compound of formula I

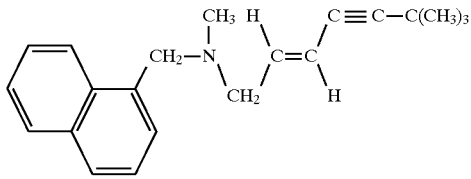

in free base form or in acid addition salt form;

2) a polymeric film former selected from the group consisting of polyvinyl acetate and methylvinylether-maleic acid monoalkyl ester copolymerisates; and 3) a solvent; and said formulation is applied to the nail in an amount sufficient to provide a dose of 0.1 to 3.0 mg of the compound of formula I per square centimeter of treated nail material.

2. A method according to claim 1 wherein the polymeric film former is polyvinyl acetate.

3. A method according to claim 1 wherein the polymeric film former is a methylvinylether-maleic acid monoalkyl ester copolymerisate.

4. The method according to claim 1 wherein the compound of formula I and the polymeric film former are present in the formulation in a ratio of about 1:0.5 to about 1:25 on a w/w basis.

5. The method according to claim 4 wherein the compound of formula I and the polymeric film former are present in the formulation in a ratio of about 1:1 to about 1:20 on a w/w basis.

6. The method according to claim 5 wherein the compound of formula I and the polymeric film former are present in the formulation in a ratio of about 1:1 to about 1:10 on a w/w basis.

7. A method according to claim 1 in which the compound of formula I comprises about 0.5% to about 30% of the formulation on a w/w basis.

8. A method according to claim 1 in which the formulation is applied once a day, every second day, or every third day.

9. The method according to claim 7 wherein the compound of formula I is present in an amount of from about 1% to about 20%.

* * * * *